US012773139B2

(12) United States Patent
Khang

(10) Patent No.: US 12,773,139 B2
(45) Date of Patent: Oct. 27, 2026

(54) PHOTOACOUSTIC DIAGNOSIS DEVICE

(71) Applicant: HME SQUARE INC., Daejeon (KR)

(72) Inventor: Yoon Ho Khang, Gyeonggi-do (KR)

(73) Assignee: HME SQUARE INC., Daejeon (KR)

( * ) Notice: Subject to any disclaimer, the term of this patent is extended or adjusted under 35 U.S.C. 154(b) by 197 days.

(21) Appl. No.: 18/852,207

(22) PCT Filed: Mar. 29, 2023

(86) PCT No.: PCT/KR2023/004203
§ 371 (c)(1),
(2) Date: Sep. 27, 2024

(87) PCT Pub. No.: WO2023/191510
PCT Pub. Date: Oct. 5, 2023

(65) Prior Publication Data
US 2025/0204815 A1 Jun. 26, 2025

(30) Foreign Application Priority Data
Mar. 31, 2022 (KR) ........................ 10-2022-0040134

(51) Int. Cl.
*A61B 5/145* (2006.01)
*A61B 5/00* (2006.01)

(52) U.S. Cl.
CPC ........ *A61B 5/14532* (2013.01); *A61B 5/0095* (2013.01); *A61B 5/7225* (2013.01);
(Continued)

(58) Field of Classification Search
CPC . A61B 5/14532; A61B 5/0095; A61B 5/7225; A61B 5/7235; A61B 2562/0204;
(Continued)

(56) References Cited

U.S. PATENT DOCUMENTS 9,220,415 B2 * 12/2015 Mandelis ............. A61B 5/0095
2020/0253513 A1 * 8/2020 Zhou .................... A61B 5/7267

FOREIGN PATENT DOCUMENTS

JP 2004-510127 4/2004
JP 2010-104858 5/2010
(Continued)

OTHER PUBLICATIONS

Zhao et al. (Glucose solution determination based on liquid photoacoustic resonance), vol. 56, No. 2 / Jan. 10, 2017 / Applied Optics (Year: 2017).*
(Continued)

*Primary Examiner* — Christian Jang
(74) *Attorney, Agent, or Firm* — Wenderoth, Lind & Ponack, L.L.P.

(57) ABSTRACT

The present disclosure discloses a photoacoustic diagnostic device. More specifically, the present invention relates to a photoacoustic diagnostic device that detects ultrasound waves generated by irradiating a biological surface with a laser to noninvasively determine blood sugar concentration, or the like in a biological body. According to an embodiment of the present invention, the photoacoustic diagnostic device is equipped with a membrane element manufactured by a micro electro mechanical system (MEMS) process, and instead of mounting an expensive FFT, or the like on a transducer for receiving an ultrasound wave signal radiated from a subject and detecting a resonance peak or using a spectrum analyzer, by detecting multiple resonance peaks through multiple transducers with different resonance frequencies and combining the resonance peaks to perform analysis on blood sugar, or the like, it is possible to provide analysis results with high accuracy that are easy to implement and low cost.

9 Claims, 5 Drawing Sheets

(52) U.S. Cl.
CPC .... *A61B 5/7235* (2013.01); *A61B 2562/0204* (2013.01); *A61B 2562/0247* (2013.01); *A61B 2562/04* (2013.01)

(58) Field of Classification Search
CPC ........ A61B 2562/0247; A61B 2562/04; A61B 5/7257
See application file for complete search history.

(56) References Cited

FOREIGN PATENT DOCUMENTS

| | | |
|---|---|---|
| JP | 2017-41824 | 2/2017 |
| KR | 10-2011-0119828 | 11/2011 |
| KR | 10-2270798 | 6/2015 |
| KR | 10-2015-0073964 | 7/2015 |
| KR | 10-2019-0063446 | 6/2019 |

OTHER PUBLICATIONS

International Search Report issued Jul. 27, 2023 in International (PCT) Application No. PCT/KR2023/004203.
Notice of Allowance issued Mar. 7, 2024 in Korean Application No. KR 10-2022-0040134.

* cited by examiner

PHOTOACOUSTIC DIAGNOSIS DEVICE

TECHNICAL FIELD

The present disclosure relates to a photoacoustic diagnostic device, and in particular, to a photoacoustic diagnostic device that detects ultrasound waves generated by irradiating a biological surface with a laser to noninvasively determine a blood sugar concentration, or the like in a biological body.

BACKGROUND ART

A photoacoustic diagnostic technology is a technology that noninvasively shapes biological body tissues using photoacoustic effects. When a short electromagnetic pulse of a laser is incident on a biological body tissue for photoacoustic diagnosis, a portion of the energy is absorbed by the tissue and converted into heat, causing instantaneous thermoelastic expansion. As a result, ultrasound waves with a wide frequency band are emitted, which can be detected from various directions by an ultrasound wave transducer and converted into images.

In the photoacoustic diagnostic technology, electromagnetic waves are converted into ultrasound waves to be detected, and thus, the photoacoustic diagnostic technology has the advantage of being able to combine the characteristics of optical imaging and ultrasound wave imaging. A contrast of a pure optical imaging technique is much higher than that of ultrasound wave imaging, but the pure optical imaging technique has the disadvantage of being limited to a certain depth from the surface of the biological body due to the high light scattering of a soft tissue. Meanwhile, ultrasound wave imaging has a high spatial resolution that can be used for fetal examination.

In addition, photoacoustic imaging can simultaneously realize high optical contrast and high spatial resolution by overcoming the low imaging depth, which is a disadvantage of optical imaging, through ultrasound wave conversion by the photoacoustic effect.

The device that implements the photoacoustic diagnostic technology roughly includes an optical unit that emits a laser and a transducer that detects and measures ultrasound waves. In addition, a method of driving the transducer that measures the ultrasound waves is divided into a piezoelectric method and an electrostatic method. Here, in the electrostatic method, the transducer is mainly manufactured using a micro electro mechanical system (MEMS).

In the piezo method, as a potential difference generated in a piezoelectric material in response to the pressure generated by the ultrasound wave, the ultrasound waves are measured by measuring the voltage. Moreover, in the electrostatic MEMS method, ultrasound waves are measured by measuring the change in electrostatic capacitance according to a change in shape of a membrane changed by the pressure of the ultrasound wave.

In particular, wildband characteristic can be said to be important for the MEMS transducer generally installed in the photoacoustic diagnostic device, and in order to obtain the wideband characteristic, the design is made in the direction of reducing a resonance peak in a frequency response curve and maximizing a flat area. This design has the advantage of being usable for a wide frequency band, but the design can be said to be disadvantageous in detecting high-sensitivity characteristics.

In addition, the conventional MEMS photoacoustic diagnostic device detects by matching a resonance frequency of the transducer to a main peak (Peak) in a photoacoustic signal when measuring blood sugar. In this case, the detected ultrasound wave signal is a time-domain signal, and for diagnosis, the time-domain signal should be converted into a frequency domain signal in which the resonance peak appears.

To this end, in the conventional acoustic diagnosis device, the conversion is performed by using a separate device called a spectrum analyzer that converts the time-domain to the frequency-domain, and then the next diagnosis procedure proceeds, which is cumbersome and delays the overall diagnosis time.

In particular, in the case of the aforementioned spectrum analyzer, when the signal of the frequency domain to be measured is mixed with an input signal when generated to extract the signal of the corresponding frequency domain, and frequency-domain data for the entire frequency domain should be measured while changing the generated signal, so the circuit structure is complicated, and there is a disadvantage that the cost increases due to this. Moreover, it is difficult to reduce of the size of the spectrum analyzer.

In addition, there is a method of converting digital data output in the time-domain within a photoacoustic diagnostic device into frequency-domain data through a fast Fourier transform (FFT). However, when using this FFT circuit, high-speed measurement is required to obtain high resolution, and since a large amount of data is required, an expensive circuit chipset is required, and there are disadvantages in that the power consumption is significantly high.

As a prior document related to this case, there is Korean Patent No. 10-2270798 (publication date: Jun. 30, 2021).

DISCLOSURE

Technical Problem

The present disclosure is designed to solve the above-mentioned problem, and the present disclosure relates to a photoacoustic diagnostic device according to a photoacoustic diagnostic technology that can noninvasively measure the state of biological body tissues using the photoacoustic effect, and an object of the present disclosure is to implement a photoacoustic diagnostic device that can secure a frequency domain signal required for analysis without using an expensive FFT circuit or spectrum analyzer.

Technical Solution

In order to achieve the object, according to an embodiment of the present disclosure, there is provided a photoacoustic diagnostic device including: a light source unit configured to irradiate a subject with light; a transducer unit configured to receive an acoustic signal radiated from the subject as the subject is irradiated with the light and output a plurality of electric signals in the form of a first domain signal, each of which includes one or more peak components; a combining unit configured to receive the plurality of electric signals, combine each of the plurality of electric signals according to a frequency band, and output a single combined signal in the form of a second domain signal; and a diagnostic unit configured to determine one or more characteristics related to an analysis target of the subject through frequencies of one or more resonance peaks included in the combined signal.

The transducer unit may include one or more transducers including a membrane element of which an electrostatic capacitance changes according to the acoustic signal, and a measuring unit electrically connected to the membrane element to measure the electrostatic capacitance.

The transducer unit may include a plurality of transducers forming one array, and in the plurality of transducers, areas of membrane elements may be different from each other.

The area of the membrane element may correspond to a frequency band of a peak component included in each of the plurality of electric signals.

The transducer unit may include at least one transducer including a piezo element configured to output an electric signal corresponding to a pressure change while vibrating according to the acoustic signal.

The photoacoustic diagnostic device may further include a conversion unit configured to receive a plurality of electric signals, filter the electric signals into different specific frequency bands, and transmit the filtering signal as an electric signal to the combining unit.

The conversion unit may include a plurality of filters configured to receive the electric signal from the transducer and pass only a frequency band corresponding to a different peak component and input the frequency band to the coupling unit.

The first domain signal may be a time-domain signal and the second domain signal may be a frequency-domain signal.

The analysis target may be blood sugar contained in a body of the subject, and the diagnostic unit may measure a blood sugar level in response to an amplitude of the resonance peak.

Advantageous Effects

According to an embodiment of the present invention, the photoacoustic diagnostic device is equipped with the membrane element manufactured by a micro electro mechanical system (MEMS) process, and instead of mounting an expensive FFT, or the like on a transducer for receiving an ultrasound wave signal radiated from a subject and detecting a resonance peak or using a spectrum analyzer, by detecting multiple resonance peaks through multiple transducers with different resonance frequencies and combining the resonance peaks to perform analysis on blood sugar, or the like, it is possible to provide analysis results with high accuracy that are easy to implement and low cost.

BEST MODE

Figure 1:
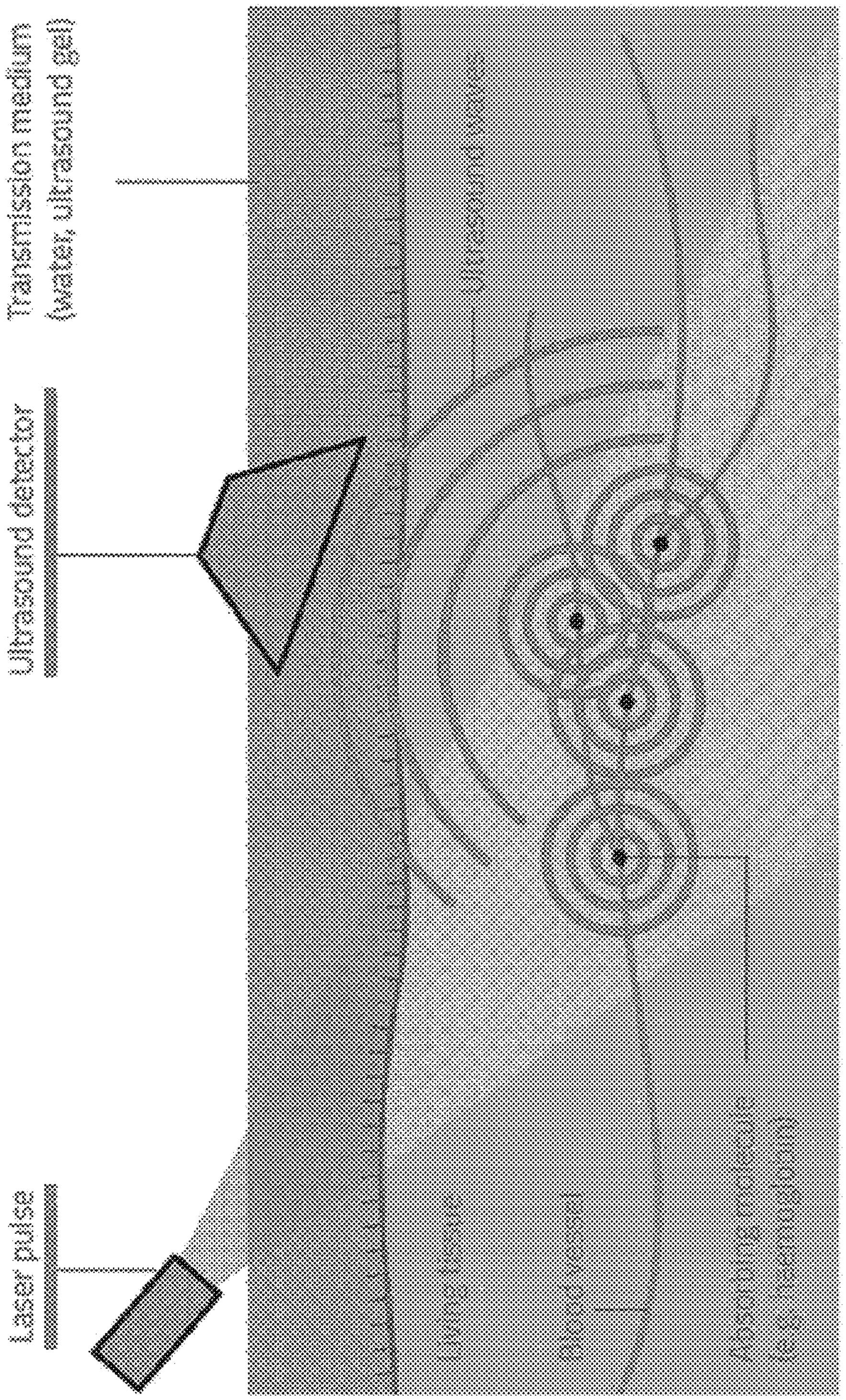
FIG. 1 is a schematic diagram illustrating a photoacoustic diagnostic technology applied to a photoacoustic diagnostic device according to one embodiment of the present disclosure.

The advantages and features of the present disclosure and the method for achieving them will become clear with reference to the embodiments described in detail below together with the attached drawings. However, the present disclosure is not limited to the embodiments disclosed below and may be implemented in various different forms, and these embodiments are provided only to make the disclosure of the present disclosure complete and to fully inform a person skilled in the art to which the present disclosure belongs of the scope of the present disclosure, and the present disclosure is defined only by the scope of the claims.

The terminology used herein is for the purpose of describing embodiments and is not intended to limit the present disclosure. In the present disclosure, the singular includes the plural unless specifically stated otherwise. The terms "comprise" or "comprising" used in the specification do not exclude the presence or addition of one or more other components other than the mentioned components. Throughout the specification, the same reference numerals refer to the same components, and include each and every combination of the components mentioned. Although the terms "first", "second", or the like are used to describe various components, these components are not limited by these terms. These terms are only used to distinguish one component from another. Therefore, it is obvious that the first component mentioned below may also be the second component within the technical concept of the present disclosure.

In addition, unless otherwise defined, all terms used in this specification may be used in a meaning that can be commonly understood by a person skilled in the art to which the present disclosure belongs. In addition, terms defined in a commonly used dictionary are not to be ideally or excessively interpreted unless explicitly specifically defined.

Hereinafter, a photoacoustic diagnostic device according to one embodiment of the present disclosure will be described in detail with reference to the drawings.

FIG. 1 is a schematic diagram illustrating a photoacoustic diagnostic technology applied to a photoacoustic diagnostic device according to one embodiment of the present disclosure.

Referring to FIG. 1, the photoacoustic diagnostic device according to the embodiment of the present disclosure may roughly include an optical means for irradiating the surface of a subject with a laser pulse, and a detection means for detecting an ultrasound wave radiated as the emitted laser pulse is absorbed by hemoglobin, or the like, in a blood vessel or interstitial fluid inside skin tissue.

Here, the optical means may be implemented as an optical section that outputs infrared light, and the detection means may be implemented as a plurality of transducers, or the like that receive an ultrasound wave signal and detect a specific resonance peak.

Hereinafter, the structure of the photoacoustic diagnostic device according to the embodiment of the present disclosure will be described in detail with reference to the drawings.

Figure 2:
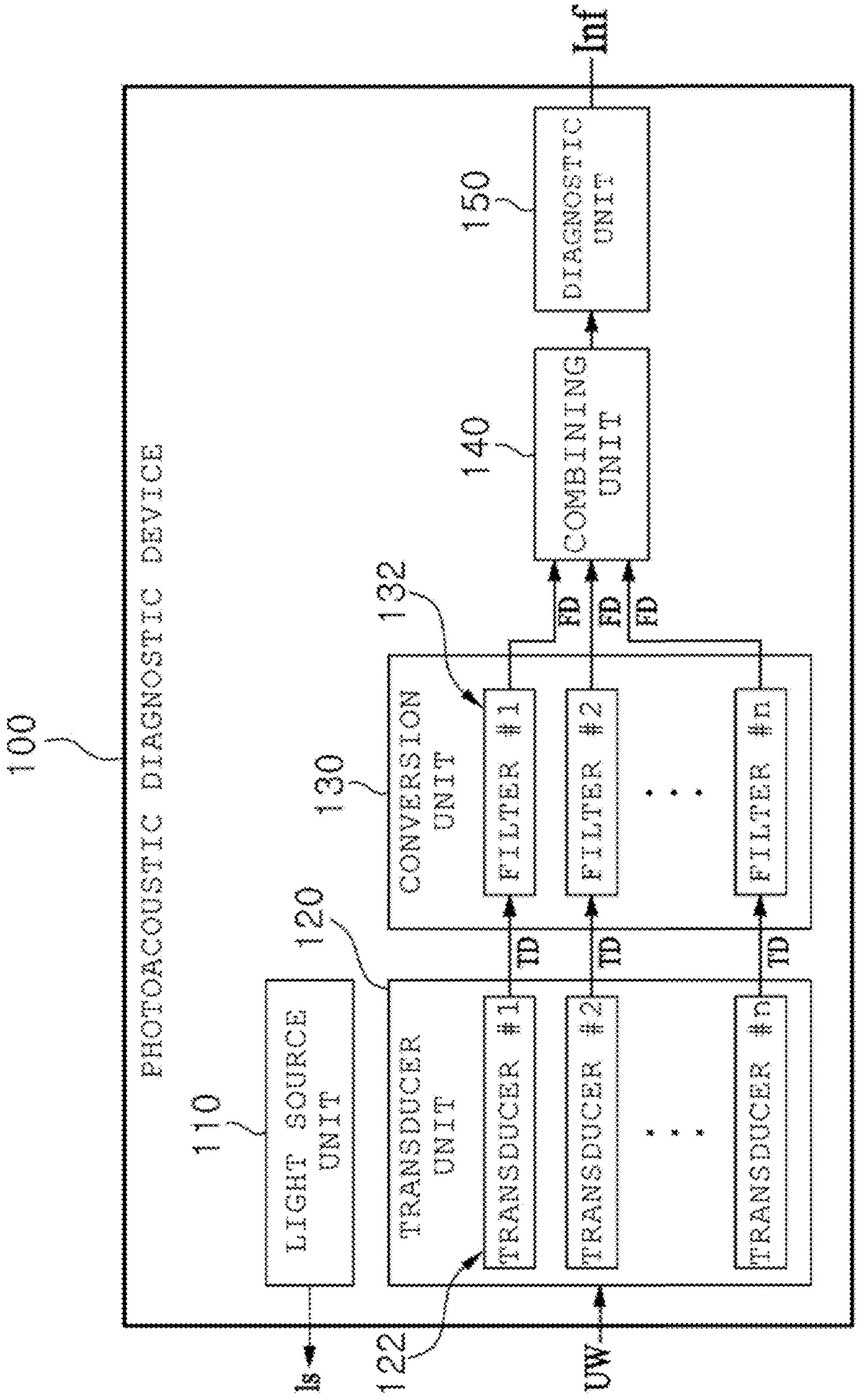
FIG. 2 is a diagram illustrating a structure of the photoacoustic diagnostic device according to one embodiment of the present disclosure.

FIG. 2 is a diagram illustrating the structure of the photoacoustic diagnostic device according to the embodiment of the present disclosure.

Referring to FIG. 2, a photoacoustic diagnostic device 100 according to one embodiment of the present disclosure may include a light source unit 110 that irradiates a subject with a light, a transducer unit 120 that receives an acoustic signal radiated from the subject as the subject is irradiated with the light and outputs a plurality of electric signals in the form of a first domain signal, a filtering conversion unit 130 that receives a plurality of electric signals, filters them each with different specific frequency bands, and outputs a plurality of filtering signals each including one peak component, a combining unit 140 that receives a plurality of filtering signals, combines each of the plurality of filtering signals according to a frequency band, and outputs a single combined signal in the form of a second domain signal, and a diagnostic unit 150 that determines one or more characteristics related to an analysis target of the subject through the frequency of one or more resonance peaks included in the combined signal.

The light source unit 110 may be arranged on one side of the photoacoustic diagnostic device and may include a predetermined infrared emitting means capable of emitting light ls, such as a solid-state laser, a semiconductor laser, or an LED. This light source unit 110 irradiates the subject surface with the laser light Is to perform the diagnosis, thereby vibrating the injection of the analysis target inside the subject in a non-invasive manner and causing the emission of an ultrasound wave signal due to the vibration.

The transducer unit 120 may use various types of transducers, such as a piezoelectric type transducer, an electrostatic type transducer, a magnetic type transducer, or an optical type transducer, and may be implemented with multiple transducers 122 depending on the frequency characteristics to be detected.

Among the various types of transducers, in a case of the piezoelectric type transducer, the plurality of transducers 122 may use a piezoelectric micromachined ultrasonic transducer (pMUT) that includes a piezo element that converts ultrasound waves and electrical signals into each other by the pressure change while vibrating, and in a case of the electrostatic transducer, the plurality of transducers 122 may use a capacitive type ultrasound wave transducer (cMUT) including a membrane element that converts ultrasound waves and electrical signals into each other by the change in electrostatic capacitance.

Here, the membrane element may be formed into a structure in which the membrane element is positioned at a corresponding position with respect to the membrane film at a predetermined distance, and through this structure, an ultrasound wave signal radiated from inside the subject may be received and a measurement signal may be output according to the change in the electrostatic capacitance. A specific description of this membrane element will be described later.

In particular, the transducer 122 according to the embodiment of the present disclosure can be equipped with multiple (#1 to #n, n is a natural number), and the detection frequency band is set differently so that each different resonance peak is detected.

In detail, an ultrasound wave signal UW radiated from the subject is received by the membrane element of each transducer 122. In this case, the electrostatic capacitance of each membrane element changes in response to the received ultrasound wave signal, and each transducer 122 may measure the amount of change in the electrostatic capacitance and output an electric signal TD including one or more peak components of different frequency bands corresponding to the area of the membrane element to the conversion unit 130. Here, the above-mentioned electric signal TD becomes a signal in the time-domain form.

The conversion unit 130 can include a plurality of filters 132 each corresponding to a frequency band set for the plurality of transducers 122. The time domain signal TD output from the transducer unit 120 may include one or more peak components and noise components, and multiple filters included in the conversion unit 130 receive the electric signal TD in the time-domain form and output a filtering signal FD that includes only a specific frequency band set to each filter 132 through a filtering process. Accordingly, each filtering signal FD may have a different band and include one resonance peak.

The conversion unit 130 may be included in the photoacoustic diagnostic device according to a designer's intention to filter the aforementioned electric signal TD, or may be omitted.

In addition, as an example, about six transducers 122 and six filters 132 may be installed, and in this case, the transducer unit 120 may detect six resonance peaks.

The combining unit 140 may receive the filtering signal FD output from the conversion unit 130 and combine the filtering signal into one signal. Each filtering signal FD may include one resonance peak, and can sequentially combine the resonance peaks according to the frequency band to generate one combined signal. The generated combined signal may be output to the diagnostic unit 150, and this combined signal becomes a signal in the frequency-domain form. Accordingly, the photoacoustic diagnostic device 100 according to the embodiment of the present disclosure may output a signal in the time-domain form and a signal in the frequency-domain form without using a separate FFT circuit or spectrum analyzer.

The diagnostic unit 150 may perform a diagnosis by measuring amplitudes of one or more resonance peaks present in the combined signal output from the combining unit 140. As an example, the photoacoustic signal generated when an infrared laser is emitted into the body illustrates the main characteristics of blood sugar. That is, when six major resonance peaks are detected when a laser is emitted into the body, it can be known that blood sugar exists in the body, and as the amplitude of the six resonance peaks increases, it is determined that the amount of blood sugar increases.

The diagnostic unit 150 may generate diagnostic information Inf according to the analysis result of the amplitude and provide the diagnostic information in the form of numerical data or graphs through a display, or the like.

According described above, the photoacoustic diagnostic device according to the embodiment of the present disclosure is equipped with multiple MEMS type transducers that detect resonant frequencies of different bands, detects one or more resonance peaks by each transducer, and generates diagnostic information such as a blood sugar level of the subject through the amplitude, thereby overcoming problems such as increased difficulty in implementing the device and high costs due to receiving an ultrasound wave signal through the conventional detection means and converting the ultrasound wave into a frequency using an FFT, spectrum analyzer, or the like.

Hereinafter, the technical idea of the present disclosure will be described in detail through an example of a membrane element structure, which is a transducer used, when an electrostatic method is applied to a photoacoustic diagnostic device according to one embodiment of the present disclosure with reference to the drawings.

Figure 3:
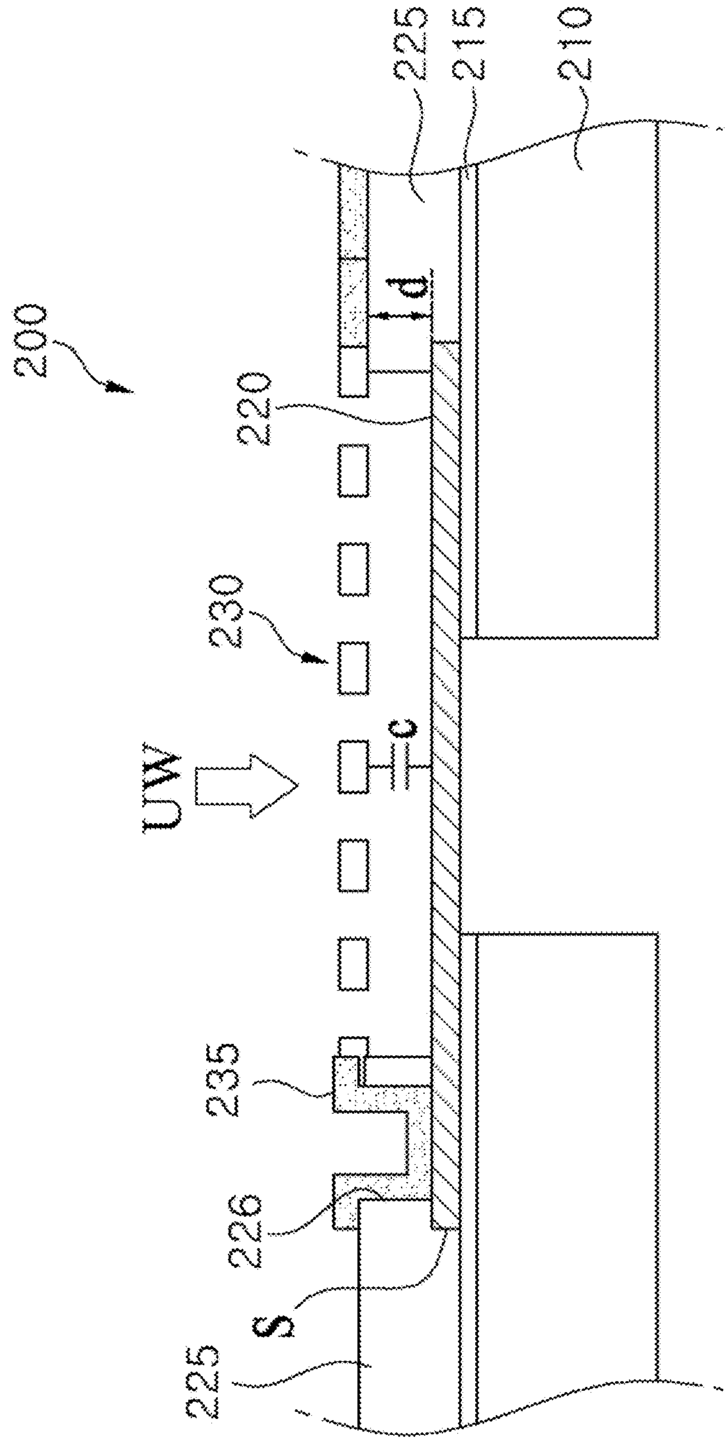
FIG. 3 is a diagram illustrating a cross-sectional structure of a membrane element mounted on the photoacoustic diagnostic device according to one embodiment of the present disclosure.

FIG. 3 is a diagram illustrating a cross-sectional structure of the membrane element mounted in the photoacoustic diagnostic device according to one embodiment of the present disclosure.

Referring to FIG. 3, a semiconductor substrate 210 mounted in a transducer according to one embodiment of the present disclosure may include a known semiconductor material, such as silicon, germanium, and silicon-germanium. Such a semiconductor material may be doped as an n-type or p-type to have conductivity, and the semiconductor substrate 210 may be a substrate processed by processing a semiconductor wafer to a predetermined thickness.

In addition, an etch-preventing layer 21 may be formed on the entire surface of the semiconductor substrate 210. This etch-protection layer 215 may include silicon nitride, for example, $Si_3N_4$, and may be formed by a chemical vapor deposition (CVD) method, for example, a low-vacuum CVD (LP CVD) or a plasma-enhanced CVD (PE CVD) method.

In addition, a membrane film 220 may be formed on the etch-protection layer 215. As an example, the membrane film 220 may be deposited over the entire surface of the etch-protection layer 215 by a chemical vapor deposition (CVD) method. The membrane film 220 may include silicon nitride, for example, $Si_3N_4$.

In addition, a portion of the semiconductor substrate 210, including the etch-protection layer 215, may be etched through an etching process using a mask to form an opening.

This opening may be formed through photolithography and an etching process. As an example, the etching process may be performed by plasma dry etching having anisotropic etching characteristics, such as reactive ion etching (RIE).

In addition, an insulating layer 225 may be formed on the membrane film 220, and an etching hole 226 exposing a portion of the membrane film 220 may be formed on the insulating layer 225. This etching hole 226 may be formed using photolithography and etching techniques.

In addition, an electrode 235 may be formed on the etching hole 226 and electrically connected to a read out integrated circuit (ROIC) included in the transducer unit so that electrostatic capacitance may be measured.

In addition, a back plate 230 having a plurality of acoustic holes formed therein may be arranged on the upper portion of the membrane film 220 at a predetermined distance d. Since the back plate 230 is not directly connected to the membrane film 220, the back plate forms a capacitor, and thereafter, when an ultrasound wave signal UW reaches the upper part of the back plate 230, the membrane film 220 vibrates through the acoustic hole, and as the distance d from the back plate 230 changes, the change in electrostatic capacitance C is measured in the ROIC.

In addition, although not illustrated, the back plate 230 may also be connected to the ROIC through a separate electrode for measuring electrostatic capacitance C.

Here, the electrostatic capacitance C of the membrane element formed between the membrane film 220 and the back plate 230 facing each other satisfies the following Mathematical Expression 1 (here, an area of the membrane film 220 and the back plate 230 is "S", a separation distance is "d", and a dielectric constant is "ε").

$$C = \varepsilon\frac{S}{d} \quad \text{[Mathematical Expression 1]}$$

Therefore, when the ultrasound wave signal UW reaches the back plate 230, vibration occurs in the membrane film 220, and by measuring the amount of change in the electrostatic capacitance C, the time domain signal for the ultrasound wave signal UW may be generated.

In addition, although not illustrated, according to one embodiment of the present disclosure, a piezoelectric piezo element may be used instead of the electrostatic membrane element described above in the transducer, and in this case, the ROIC may be configured to measure the pressure change of the piezoelectric piezo element to generate a time domain signal for the ultrasound wave signal UW.

Hereinafter, a method of performing a signal processing procedure in a photoacoustic diagnostic device according to one embodiment of the present disclosure will be described in detail with reference to FIGS. 4 and 5.

Figure 4:
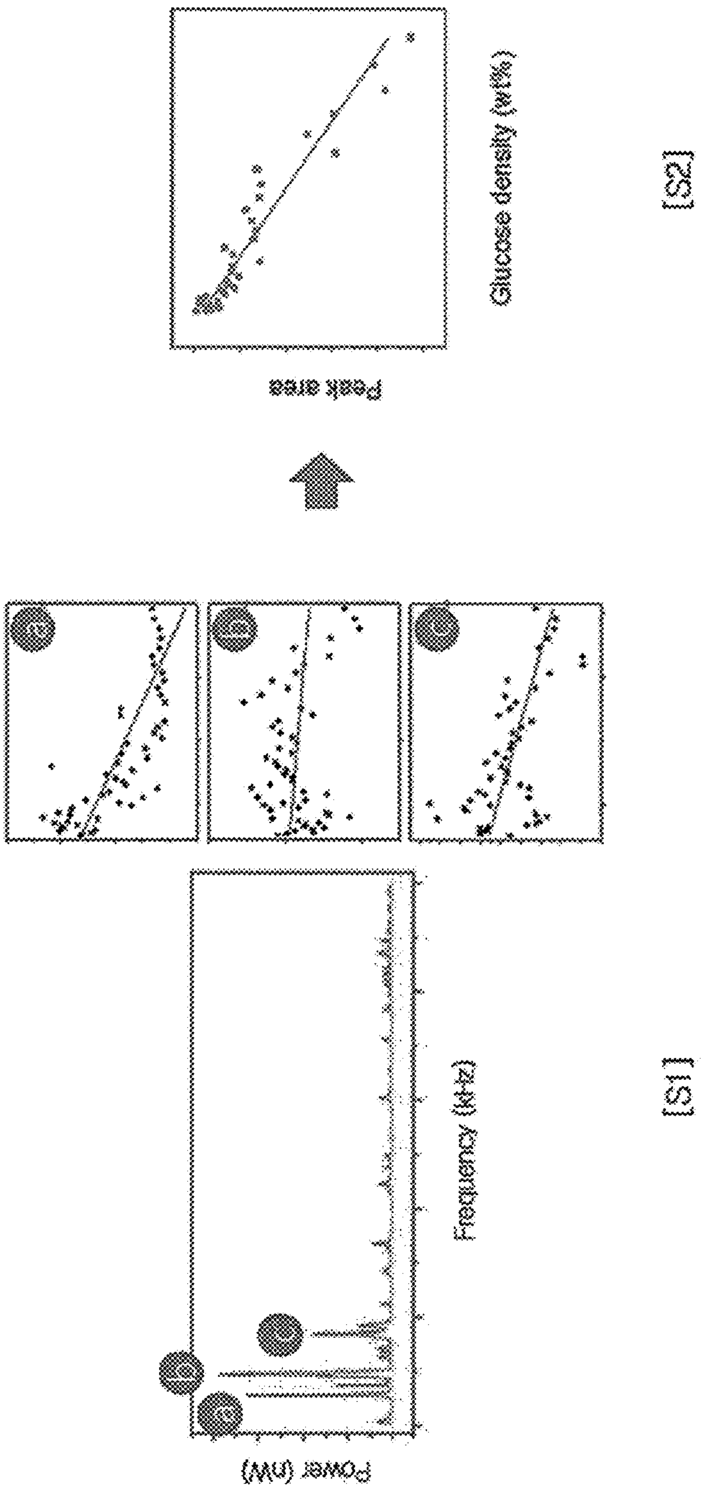
FIG. 4 is a diagram illustrating a data processing method by the photoacoustic diagnostic device according to one embodiment of the present disclosure.
Figure 5:
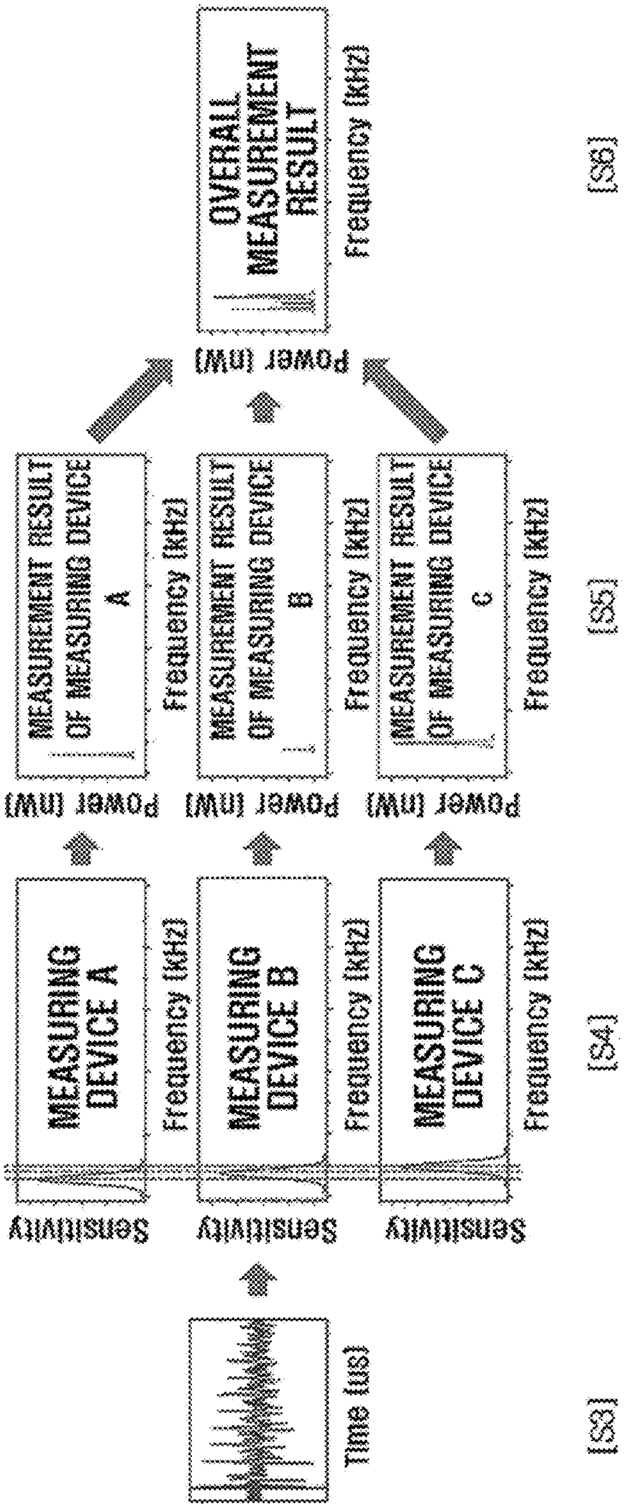
FIG. 5 is a diagram illustrating a data processing method when a filter is applied to the photoacoustic diagnostic device according to one embodiment of the present disclosure.

FIG. 4 is a diagram illustrating a data processing method by the photoacoustic diagnostic device according to one embodiment of the present disclosure, and FIG. 5 is a diagram illustrating a data processing method when a filter is applied to the photoacoustic diagnostic device according to one embodiment of the present disclosure.

Referring to FIG. 4, an ultrasound wave signal radiated by the laser light emitted to the subject is generally a time domain signal, and when the ultrasound wave signal is converted into a frequency signal using an FFT circuit or the like, according to the embodiment of [S1], at least one of resonance peaks of A, B, or C components exist in a predetermined frequency band. The shapes of these resonance peaks, A, B, or C, are related to blood sugar levels in the body, and by detecting these resonance peaks, A, B, or C, the blood sugar levels of the subject can be analyzed.

In particular, the photoacoustic device according to the embodiment of the present disclosure can improve the measurement result by coupling or combining the resonance peaks through the combining unit, and as exemplified in [S2], the blood sugar density can be measured by combining the signal points included in the frequency corresponding to each of the resonance peaks A, B, and C, and the result can be improved.

In addition, referring to FIG. 5, as described above, the ultrasound wave signal received by the photoacoustic diagnostic device according to the embodiment of the present disclosure is the time domain signal, and in order to analyze the time domain signal, it is required to change into the form of a frequency domain signal.

To this end, according to the embodiment of the present disclosure, instead of using a DFT or FFT circuit for signal conversion, a plurality of measuring devices (transducers and filters) are used to measure and filter the peak components that appear in different frequency bands in the input time domain signal, thereby outputting only the signal of the band required for analysis.

In addition, each filtered signal may be combined into one signal for analysis according to the frequency band again. When three measuring devices are used, the combined signal having three resonance peaks may be generated, and this combined signal is not a signal converted through an FFT circuit, but may be used for waveform analysis in the form of the frequency-domain.

Although many matters are specifically described in the above description, this should be interpreted as an example of a preferred embodiment rather than limiting the scope of the invention. Therefore, the invention should not be defined by the described embodiments, but by the claims and their equivalents.

The invention claimed is:

1. A photoacoustic diagnostic device comprising:

a light source unit configured to irradiate a subject with a light;

a transducer unit configured to receive an acoustic signal radiated from the subject as the subject is irradiated with the light and output a plurality of electric signals in the form of a first domain signal, each of which includes one or more peak components;

a combining unit configured to receive the plurality of electric signals, combine each of the plurality of electric signals according to a frequency band, and output a single combined signal in the form of a second domain signal; and a diagnostic unit configured to determine one or more characteristics related to an analysis target of the subject through frequencies of one or more resonance peaks included in the combined signal.

2. The photoacoustic diagnostic device of claim 1, wherein the transducer unit includes one or more transducers including a membrane element of which an electrostatic capacitance changes according to the acoustic signal, and a measuring unit electrically connected to the membrane element to measure the electrostatic capacitance.

3. The photoacoustic diagnostic device of claim 2, wherein the transducer unit includes a plurality of transducers forming one array, and in the plurality of transducers, areas of membrane elements are different from each other.

4. The photoacoustic diagnostic device of claim 3, wherein the area of the membrane element corresponds to a frequency band of a peak component included in each of the plurality of electric signals.

5. The photoacoustic diagnostic device of claim 1, wherein the transducer unit includes at least one transducer including a piezo element configured to detect a pressure change while vibrating according to the acoustic signal, and a measuring unit electrically connected to the piezo element to measure the pressure change.

6. The photoacoustic diagnostic device of claim 1, further comprising a conversion unit configured to receive a plurality of electric signals from the transducer, filter the electric signals into different specific frequency bands, and transmit the filtering signal as an electric signal to the combining unit.

7. The photoacoustic diagnostic device of claim 6, wherein the conversion unit includes a plurality of filters configured to receive the electric signal from the transducer and pass only a frequency band corresponding to a different peak component and input the frequency band to the coupling unit.

8. The photoacoustic diagnostic device of claim 1, wherein the first domain signal is a time-domain signal and the second domain signal is a frequency-domain signal.

9. The photoacoustic diagnostic device of claim 1, wherein the analysis target is blood sugar contained in a body of the subject, and the diagnostic unit measures a blood sugar level in response to an amplitude of the resonance peak.

* * * * *